(12) United States Patent
Tseng et al.

(10) Patent No.: US 9,127,984 B2
(45) Date of Patent: Sep. 8, 2015

(54) SERS-ACTIVE STRUCTURE, FABRICATION METHOD THEREOF, AND SERS SYSTEM COMPRISING THE SAME

(71) Applicant: NATIONAL TSING HUA UNIVERSITY, Hsinchu (TW)

(72) Inventors: Fan-Gang Tseng, New Taipei (TW); Teng-Feng Kuo, Taipei (TW); Tsung-Yen Lee, New Taipei (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 73 days.

(21) Appl. No.: 13/749,699

(22) Filed: Jan. 25, 2013

(65) Prior Publication Data

US 2014/0043605 A1 Feb. 13, 2014

(30) Foreign Application Priority Data

Aug. 9, 2012 (TW) .............................. 101128798 A (51) Int. Cl.
| | |
|---|---|
| *G01J 3/44* | (2006.01) |
| *G01J 1/58* | (2006.01) |
| *H03F 17/00* | (2006.01) |
| *B05D 7/22* | (2006.01) |
| *B32B 3/10* | (2006.01) |
| *G01N 21/65* | (2006.01) |

(52) U.S. Cl.
CPC .................. *G01J 3/44* (2013.01); *G01N 21/658* (2013.01)

(58) Field of Classification Search
CPC ....... G01J 3/44; G01N 21/658; G01N 21/554; G01N 21/648; G01N 21/64; G01N 21/47
USPC ............. 356/301; 250/458; 330/59; 427/230; 428/138
See application file for complete search history.

(56) References Cited

U.S. PATENT DOCUMENTS

2008/0304060 A1* 12/2008 Naya .............................. 356/301
2009/0213369 A1 8/2009 Lee et al.

FOREIGN PATENT DOCUMENTS

TW 201116819 A1 5/2011

OTHER PUBLICATIONS

Teng-Feng Kuo, Fan-Gang Tseng, "Highly Uniform and Reproducible Surface Enhanced Raman Scattering From Double Nanoshelled Gold Nanoparticles (DNS-GNP) Arrays with Tunable Interior Nanogap", published on Symposium on Engineering Medicine and Biology Applications&International workshop on Bio-inspired Systems and Prosthetic Devices, Feb. 11-13, 2012, Taichung, Taiwan.
Teng-Feng Kuo et al., "Highly Uniform Surface Enhanced Raman Scattering From Double Nanoshelled Gold Nanoparticles (DNS-GNP) Arrays with Tunable Interior Nanogap", published on the 4th International Symposium on Microchemistry and Microsystems (ISMM), Jun. 10-13, 2012, Hsinchu, Taiwan.

* cited by examiner

*Primary Examiner* — Tarifur Chowdhury
*Assistant Examiner* — Sunghee Y Gray
(74) *Attorney, Agent, or Firm* — CKC & Partners Co., Ltd.

(57) ABSTRACT

A SERS-active structure includes a substrate, at least one metal nanoparticle, a dielectric layer and a metal nanolayer. The metal nanoparticles are disposed on the substrate. The substrate and the metal nanoparticles are covered by the dielectric layer, so that the dielectric layer forms a recessed portion with a dihedral angle formed by a surface of the dielectric layer at which the at least one metal nanoparticle contacts the substrate. The dielectric layer is covered by the metal nanolayer and the metal nanolayer has a gap located at and exposing the recessed portion.

20 Claims, 8 Drawing Sheets

SERS-ACTIVE STRUCTURE, FABRICATION METHOD THEREOF, AND SERS SYSTEM COMPRISING THE SAME

RELATED APPLICATIONS

This application claims priority to Taiwan Patent Application Serial Number 101128798, filed Aug. 9, 2012, which is herein incorporated by reference.

BACKGROUND

1. Field of Invention

The present disclosure relates to an active structure. More particularly, the present disclosure relates to a surface-enhanced Raman scattering (SERS)-active structure, a method for fabricating the SERS-active structure, and a SERS system comprising the SERS-active structure.

2. Description of Related Art

Surface-enhanced Raman scattering (SERS) is a technique concerning surface effects. The SERS technique is able to significantly enhance the Raman signal from analyte molecules, by such as adsorbed or adjacently jointed over a metal surface. In this regard, a structure is capable of enhancing the Raman signal of the analyte molecules over the metal surface is so called a SERS-active structure.

The SERS technique mainly applies the property of nanoscale metal materials which introduce local plasmonic field enhancement. In principle, the nanoscale metal materials, after being irradiated by a radiation source, have a surface plasmon resonance with the radiation and exhibit aggregation and oscillation of electrons at localized spot, so as to generate a strong plasmonic field in a near field. In general, the position of the strong plasmonic field is known as hot spots.

Compared to traditional Raman scattering, the SERS technique is better at trace measurement and surface specificity, such that it has broader applications. However, both occurrence of surface effects and the enhancement of Raman signal are strongly affected by the surface structure of the metals where analyte molecules adsorbed or are adjacent to. This is why a SERS-active structure itself and a fabrication method thereof play such a crucial role in the SERS technique.

With the conventional SERS-active structure, the generated hot spots have drawbacks narrow scope and unconcentrated distribution. Conventional fabrication methods for the SERS-active structures such as electron beam lithography and focused ion beam milling are at high cost but low yield because of the requirements of complicated steps and expensive apparatus.

SUMMARY

According to one aspect of the present disclosure, a SERS-active structure includes a substrate, at least one metal nanoparticle, a dielectric layer, and a metal nanolayer. The at least one metal nanoparticle is disposed on the substrate. The dielectric layer covers the substrate and the at least one metal nanoparticle. The dielectric layer comprises a recessed portion and the recessed portion is with a dihedral angle formed by a surface of the dielectric layer at which the at least one metal nanoparticle contacts the substrate. The metal nanolayer covers the dielectric layer and comprises a gap. The gap is located at and exposing the recessed portion.

According to another aspect of the present disclosure, a method for fabricating a SERS-active structure includes the following steps. A substrate is provided and at least one metal nanoparticle is disposed on the substrate. A dielectric layer is formed to cover the substrate and the at least one metal nanoparticle, wherein the dielectric layer comprises a recessed portion with a dihedral angle formed by a surface of the dielectric layer at which the at least one metal nanoparticle contacts the substrate. A metal nanolayer is formed to cover the dielectric layer, wherein the metal nanolayer comprises a gap located at and exposing the recessed portion.

According to the other aspect of the present disclosure, a SERS system includes an analyte stage, a radiation source, and a detector. The analyte stage is with a SERS-active structure. The SERS-active structure is the same as the foregoing SERS-active structure of one aspect of the present disclosure. The radiation source is configured to irradiate the SERS-active structure to generate a plasmonic field. The detector is configured to detect Raman-scattered photons which occur in the plasmonic field.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
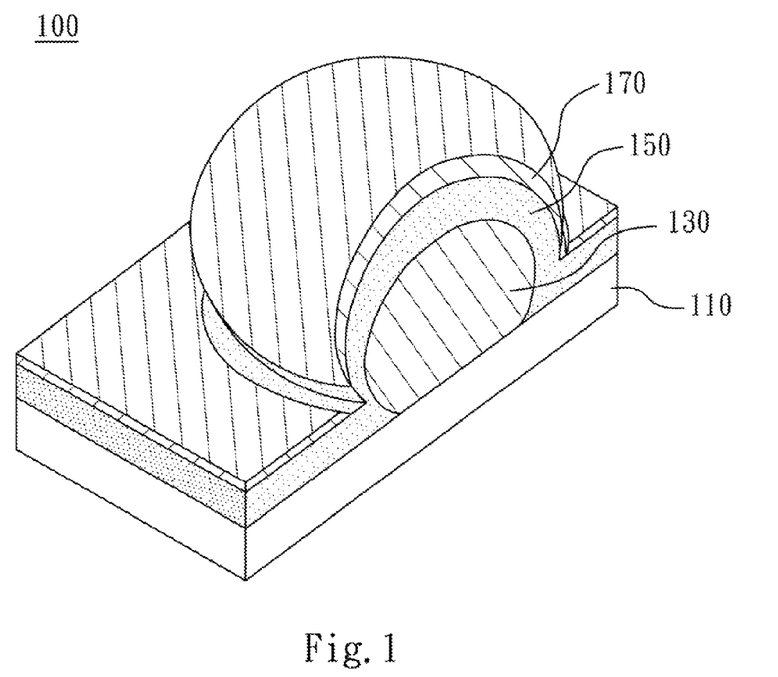
FIG. 1 is a partial schematic view showing a SERS-active structure according to one embodiment of the present disclosure.
Figure 2:
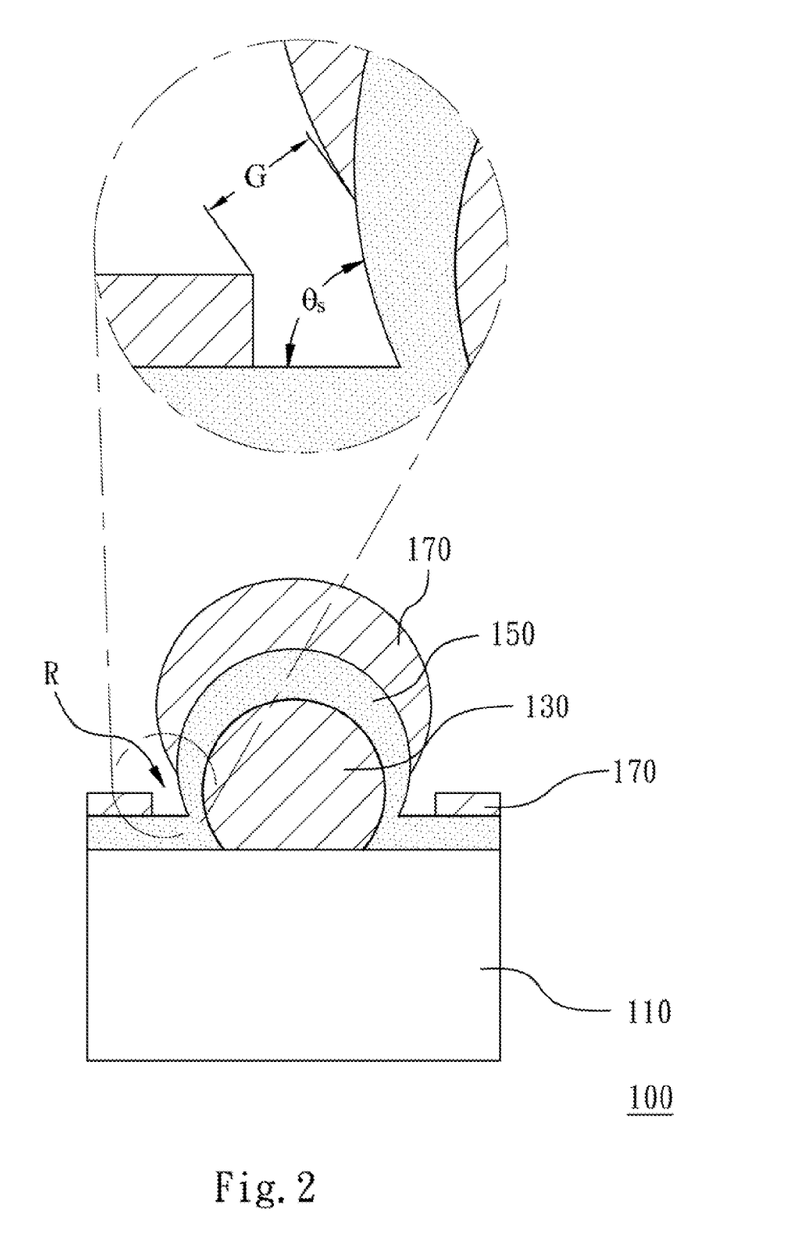
FIG. 2 is a sectional view of FIG. 1.

FIG. 1 is a partial schematic view showing a SERS-active structure according to one embodiment of the present disclosure. FIG. 2 is a sectional view of FIG. 1. Please refer to FIG. 1 and FIG. 2, a SERS-active structure 100 includes a substrate 110, at least one metal nanoparticle 130, a dielectric layer 150, and a metal nanolayer 170 (i.e. a metal layer in nanoscale). The at least one metal nanoparticle 130 is disposed on the substrate 110. The dielectric layer 150 covers the substrate 100 and the at least one metal nanoparticle 130, so that the dielectric layer 150 forms a recessed portion R which has a dihedral angle $\theta_s$. That is to say, the dielectric layer 150 includes a recessed portion R with a dihedral angle $\theta_s$ formed by a surface of the dielectric layer 150 where the at least one metal nanoparticle 130 contacts the substrate 110. The metal nanolayer 170 covers the dielectric layer 150 and has a gap G located at and exposing the recessed portion R. The dihedral angle $\theta_s$ is less than 90 degrees, and the metal nanolayer 170 is a discontinuous layer rather than a continuous layer because of the gap G.

Electronic interference between the at least one metal nanoparticle 130 and the metal nanolayer 170 can be effectively avoided because the dielectric layer 150 formed therebetween has a high dielectric constant. A strong and concentrated plasmonic field, i.e., the hot spots will be generated along the ring-shaped space constructed by the gap G when surface plasmon resonance occur by irradiating the SERS-active structure 100 with a foreign radiation source. For this reason, the strength of Raman signal of analyte molecules adsorbed onto or placed adjacent to the SERS-active structure 100 can be increased. In some embodiments of the present disclosure, the dihedral angle $\theta_s$ may also be greater than 90° as long as the gap G is located at and exposing the recessed portion R.

Figure 3:
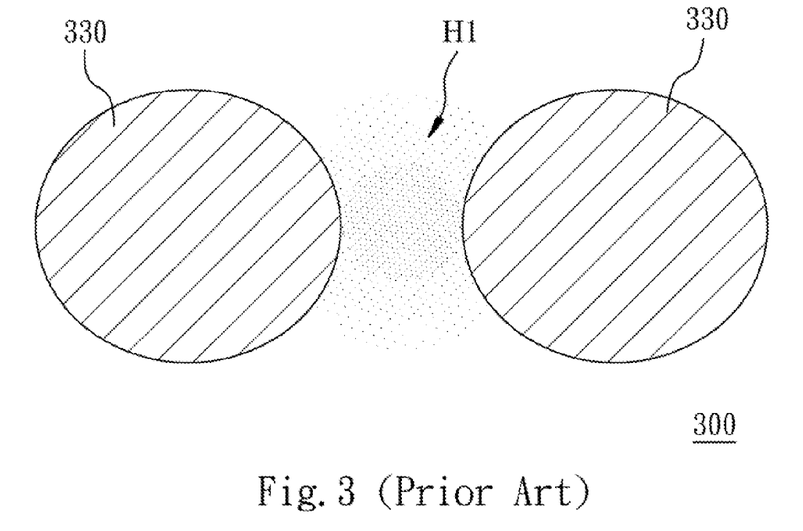
FIG. 3 is a schematic view showing the hot spots generated by a conventional SERS-active structure.
Figure 4:
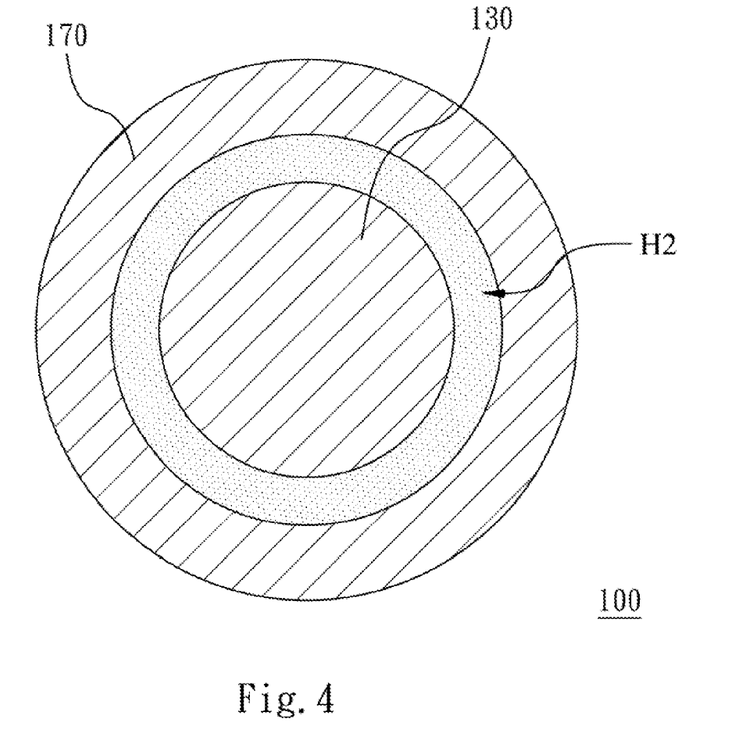
FIG. 4 is a schematic view showing the hot spots generated by a SERS-active structure of FIG. 1.

FIG. 3 is a schematic view showing the hot spots generated by a conventional SERS-active structure. FIG. 4 is a schematic view showing the hot spots generated by a SERS-active structure of FIG. 1. The conventional SERS-active structure 300 in FIG. 3 is a structure which only has nanoparticles 330 on its substrate. Referring to FIG. 3 and FIG. 4, the hot spots H1 generated by a conventional SERS-active structure 300 is narrow in scope and unconcentrated in distribution. By contrast, the hot spots H2 generated by the SERS-active structure 100 is wide and concentrated.

In the conventional SERS-active structure 300, a gap where the hot spots are generated is formed between nanoparticles 330, and is large. By contrast, the gap (not numbered) of the metal nanolayer 170 of the SERS-active structure 100 is only few nanometers to tens of nanometers. From geometry point of view, the gap of the conventional SERS-active structure 300 is presented as a point but the gap of the SERS-active structure 100 is presented as a plane (ring-shaped). Therefore, the SERS-active structure 100 can generate a stronger and more concentrated plasmonic field for enhancing Raman signal of the analyte molecules thereon than the conventional one.

Figure 5:
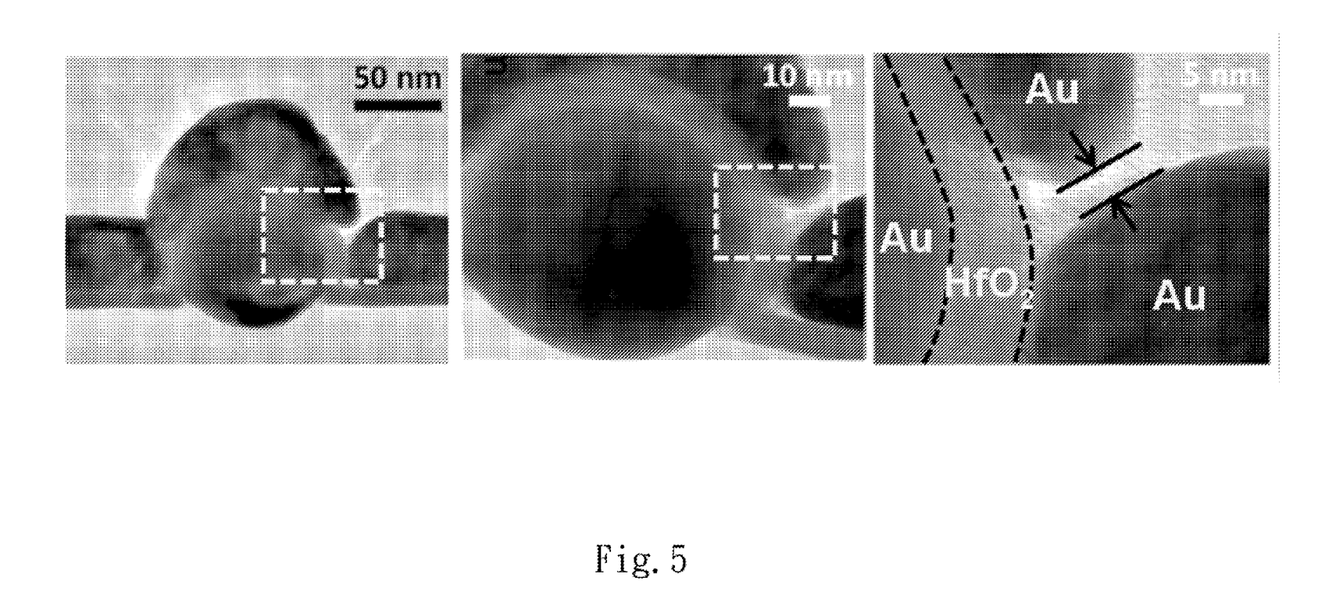
FIG. 5 is a transmission electron microscope (TEM) image of a SERS-active structure according to one embodiment of the present disclosure.

FIG. 5 is a transmission electron microscope (TEM) image of a SERS-active structure according to one embodiment of the present disclosure. In this embodiment, a SERS-active structure 100 includes a substrate 110 made of silicon, at least one metal nanoparticle 130 made of gold, a dielectric layer 150 made of hafnium dioxide ($HfO_2$), and a metal nanolayer 170 made of gold. The at least one metal nanoparticle 130 is a sphere shape of which a diameter is about 60-70 nm. The thickness of the dielectric layer 150 is about 10 nm and a gap G of the metal nanolayer 170 has a minimum width of 5 nm.

Figure 6:
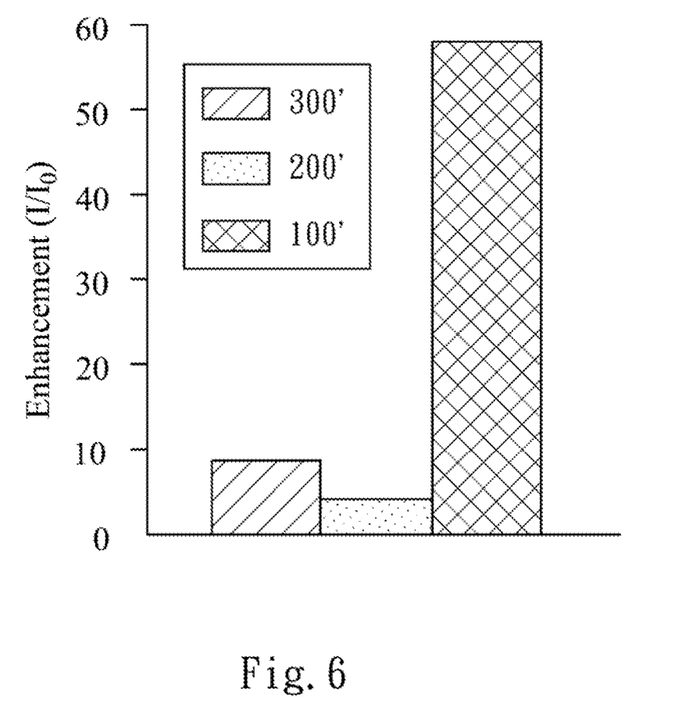
FIG. 6 is a bar chart showing Raman signal enhancement of different SERS-active structures.

FIG. 6 is a bar chart showing Raman signal enhancement of different SERS-active structures. A conventional SERS-active structure 300' has only gold nanoparticles disposed on a silicon substrate. A semi-finished SERS-active structure 200' according to one embodiment of the present disclosure has gold nanoparticles disposed on a silicon substrate, and a hafnium dioxide layer covering the gold nanoparticles and the silicon substrate. A SERS-active structure 100' according to one embodiment of the present disclosure has gold nanoparticles disposed on a silicon substrate, a hafnium dioxide layer covering the gold nanoparticles and the silicon substrate, and a gold nanolayer covering the hafnium dioxide layer.

First of all, 250 µM of rhodamine 6G (R6G) solution was applied on the structure 300', the structure 200', the structure 100', and a clear silicon substrate, respectively. Then, a radiation having a wavelength of 632.8 nm was focused by an optical lens to irradiate drops of the R6G solution on those substrates for 5 seconds. Finally, an enhancement of Raman shift at 1513 $cm^{-1}$ was calculated by a formula $I/I_0$. In the formula, $I_0$ is strength of Raman signal obtained by the clear silicon substrate and I is strength of Raman signal obtained by the structure 300', the structure 200', and the structure 100', respectively. It is obvious from FIG. 6 that enhancement of the structure 100' is much higher than that of the structure 300' or the structure 200'.

In some embodiments of the present disclosure, the at least one metal nanoparticle 130 deposed on the substrate 110 may also be a polyhedron shape as long as a recessed portion R with a dihedral angle $\theta_s$ will be formed upon the dielectric layer 170 covering the at least one metal nanoparticle 130 and the substrate 110. Moreover, the at least one metal nanoparticle 130 may be plural and arranged in an array on the substrate 110. The at least one metal nanoparticle 130 and the metal nanolayer 170 may be made of different material, for example, the at least one metal nanoparticle 130 may be made of god and the metal nanolayer 170 may be made of silver. The thickness of the dielectric layer 150 is typically less than 20 nm and the gap G of the metal nanolayer 170 has a minimum width typically less than 20 nm. Other materials for making a SERS-active structure 100 of the present disclosure may refer to a fabrication method recited as follows.

Figure 7A:
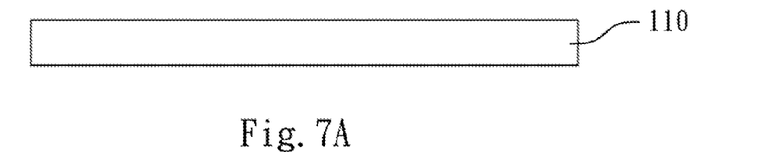
FIG. 7A-7G are schematic views showing steps to fabricate a SERS-active structure of FIG. 1.
Figure 7B:
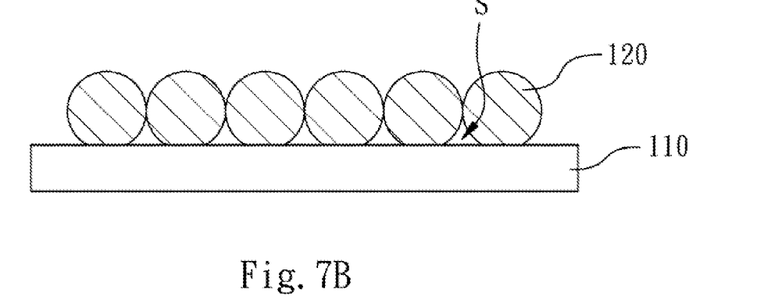

FIG. 7A-7G are schematic views showing steps to fabricate a SERS-active structure of FIG. 1. The first step is to provide the substrate 110 (as shown in FIG. 7A) and the substrate 110 may be made of fused silica, sapphire, silicon, GaAs、ZnS、CdSe、Al2O3、Ti、Ni、Cr、Al or Cu. The second step is to form a plurality of polymer particles 120 on the substrate 110 by Langmuir-Blodgett method (as shown in FIG. 7B). The polymer particles 120 are self-assembly and adjacent to each other, so that an interspace S exists between every two polymer particles 120. The polymer particles 120 are arranged in an array on the substrate 110, so that the interspaces S are in a form of array on the substrate 110. The polymer particles 120 may be polystyrene beads, each of which has a diameter approximate 400 nm. The interspace S may have a size about tens of nanometers.

Figure 7C:
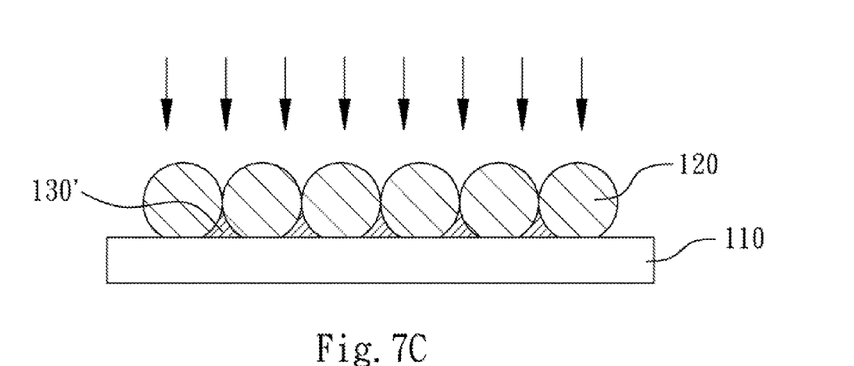
Figure 7D:
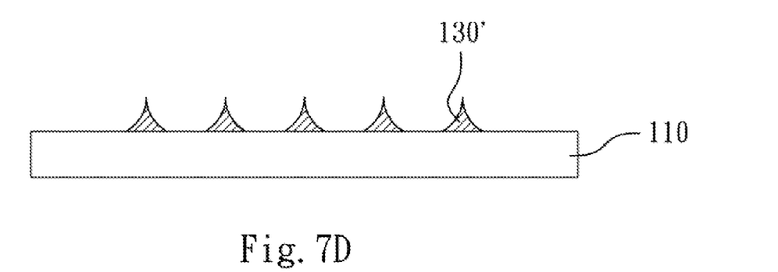

The third step is to deposit a metal material 130' by physical vapor deposition such as electron gun evaporation to fill up every interspace S (as shown in FIG. 7C). The metal material 130' may be made of precious metals or transition metals including but not limited to Au、Ag、Cu、Al、Fe、Co、Ni、Ru、Rh、Pd and Pt. The fourth step is to remove the polymer particles 120 from the substrate 110, for example, by lift-off process (as shown in FIG. 7D).

Figure 7E:
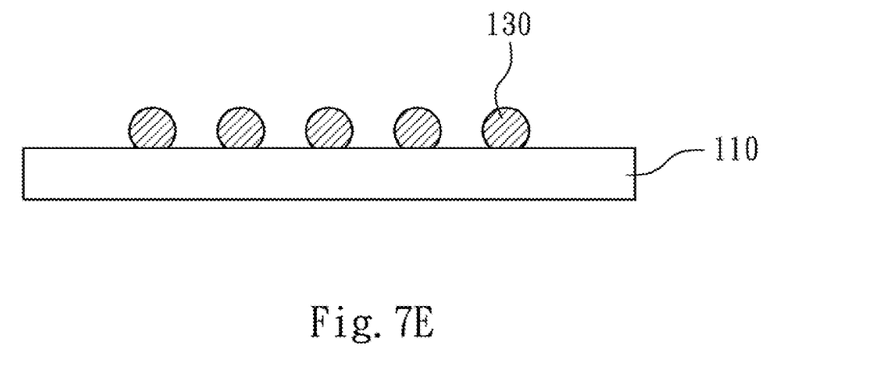
Figure 7F:
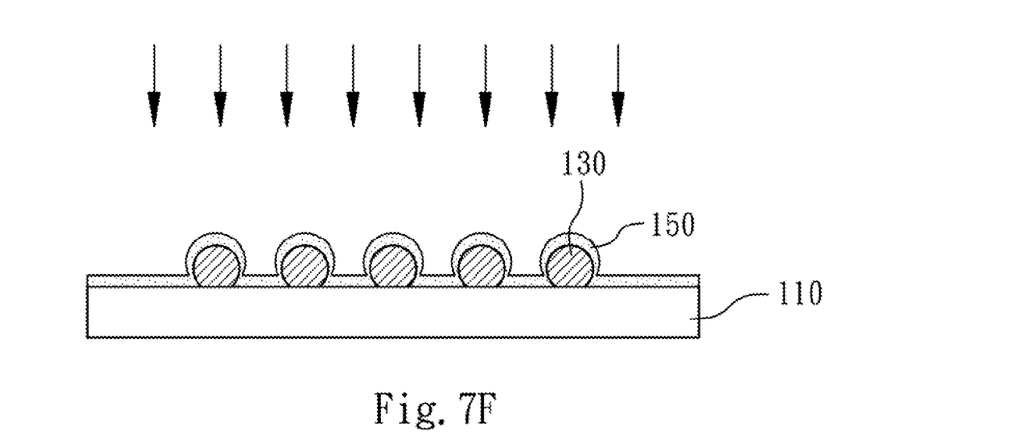

The fifth step is to anneal the metal material 130' and the substrate 110 to transform the metal material 130' on the substrate 110 into the metal nanoparticles 130 (as shown in FIG. 7E). Conditions for annealing may be 850° C. for 2 hours and each of the metal nanoparticles 130 is a sphere shape with a diameter about 60-70 nm. The metal nanoparticles 130 are in a form of array on the substrate 110 because the interspaces S are in a form of array. The sixth step is to form the dielectric layer 150 by chemical vapor deposition such as atomic layer deposition (ALD) to cover the substrate 110 and the metal nanoparticles 130 (as shown in FIG. 7F). A thickness of the dielectric layer 150 is typically less than 20 nm, preferably less than 10 nm, and more preferably less than 1 nm. The dielectric layer 150 may be made of a material with high dielectric constant such as hafnium dioxide, CuO or ZnO.

In some embodiments of the present disclosure, any materials adapted to atomic layer deposition can be used for forming the dielectric layer 150. The dielectric layer 150 has a recessed portion R (refer to FIG. 1) less than 90° because the dielectric layer 150 is very thin and covers the substrate 110 and the metal nanoparticles 130 which is a sphere shape.

Figure 7G:
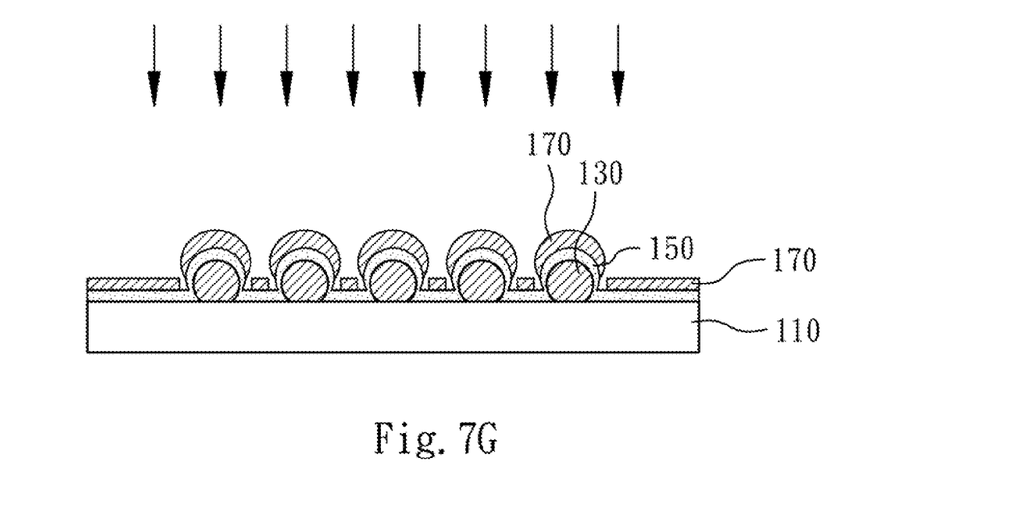

The final step is to form the metal nanolayer 170 by aligned physical vapor deposition such as electron gun evaporation to cover the dielectric layer 150 (as shown in FIG. 7G). The metal nanolayer 170 has a gap G formed and located at and exposing the recessed portion R (refer to FIG. 1) because a portion of the dielectric layer 150 covering the upper surface of the metal nanoparticles 130 shelters the recessed portion R during aligned deposition. The gap G has a minimum width typically less than 20 nm and preferably less than 5 nm. The metal nanolayer 170 may be made of precious metals or transition metals including but not limited to Au、Ag、Cu、Al、Fe、Co、Ni、Ru、Rh、Pd and Pt.

Because a great quantity of the metal nanoparticles 130 are deposed in an array on the substrate 110 and the gap G the metal nanolayer 170 has are formed during aligned deposition without an additional process. As a result, fabrication of the SERS-active structure 100 is easy, rapid and high-yield.

In some embodiments of the present disclosure, the thickness of the dielectric layer 150 is based on no tunneling effect occurred between the metal nanoparticles 130 and the metal nanolayer 170. The polymer particles 120 are not required as long as the metal nanoparticles 130 can be disposed in an array on the substrate 110. Furthermore, the metal nanoparticles 130 may be other shape rather than a sphere shape and the thickness of the dielectric layer 150 may be more than 20 nm, as long as the recessed portion R with a dihedral angle $\theta_s$ can be formed after the dielectric layer 150 covers the metal nanoparticles 130 and the substrate 110, and the gap G the metal nanolayer 170 has can be directly formed during aligned deposition.

Figure 8:
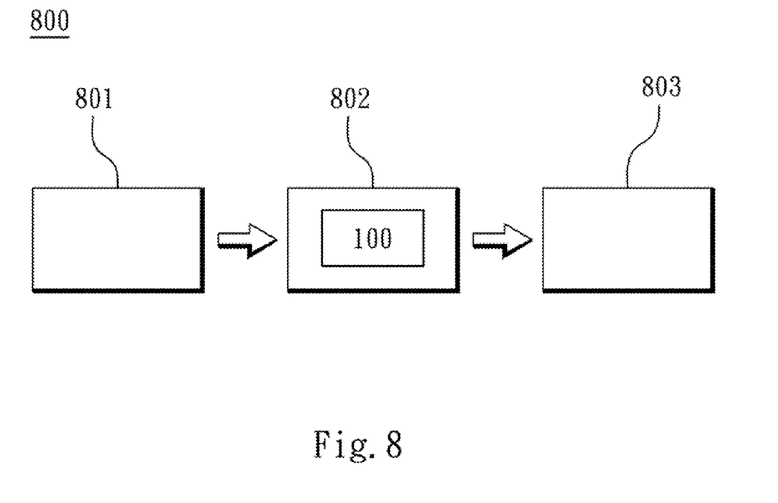
FIG. 8 is a schematic view showing a SERS system according to one embodiment of the present disclosure.

FIG. 8 is a schematic view showing a SERS system according to one embodiment of the present disclosure. A SERS system 800 includes a radiation source 801, an analyte stage 802 and a detector 803. The analyte stage 802 includes the SERS-active structure 100. Users can apply a sample on the SERS-active structure 100 of the analyte stage 802 and irradiate either of the SERS-active structure 100 and the analyte stage 802 by the radiation source 801 to generate a plasmonic field. Raman-scattered photons are occurred because analyte molecules in the sample adsorbed onto or adjacent to the SERS-active structure 100 couples the plasmonic field. The detector 803 receives and detects the Raman-scattered photons, and then the specific spectrum of analyte molecules is presented.

In some embodiments of the present disclosure, the SERS system 800 may further include various optical, components positioned between the radiation source 801 and the analyte stage 802 or between the analyte stage 802 and the detector 803. The optical components may be lens, filter or splitter.

Although the present disclosure has been described in considerable detail with reference to certain embodiments thereof, other embodiments are possible. Therefore, their spirit and scope of the appended claims should no be limited to the description of the embodiments container herein.

It will be apparent to those skilled in the art that various modifications and variations can be made to the structure of the present disclosure without departing from the scope or spirit of the invention. In view of the foregoing, it is intended that the present disclosure cover modifications and variations of this invention provided they fall within the scope of the following claims.

What is claimed is:

1. A surface-enhanced Raman scattering (SERS)-active structure, comprising:
    a substrate;
    at least one metal nanoparticle disposed on the substrate;
    a dielectric layer covering the substrate and the at least one metal nanoparticle, the dielectric layer comprising:
    a recessed portion with a dihedral angle formed by a surface of the dielectric layer at which the at least one metal nanoparticle contacts the substrate; and
    a metal nanolayer covering the dielectric layer, the metal nanolayer comprising:
    a gap located at and exposing the recessed portion.

2. The SERS-active structure of claim 1, wherein the dihedral angle is an acute angle.

3. The SERS-active structure of claim 1, wherein the gap has a minimum width less than 20 nm.

4. The SERS-active structure of claim 1, wherein the gap has a minimum width less than 5 nm.

5. The SERS-active structure of claim 1, wherein the dielectric layer is made of hafnium dioxide.

6. The SERS-active structure of claim 1, wherein a thickness of the dielectric layer is less than 20 nm.

7. The SERS-active structure of claim 1, wherein a thickness of the dielectric layer is less than 10 nm.

8. The SERS-active structure of claim 1, wherein a diameter of the at least one metal nanoparticle is in a range of about 60-70 nm.

9. The SERS-active structure of claim 1, wherein the at least one metal nanoparticle is a plurality of metal particles, and the plurality of metal particles are arranged in an array on the substrate.

10. The SERS-active structure of claim 1, wherein the at least one metal nanoparticle is made of precious metals or transition metals.

11. The SERS-active structure of claim 1, wherein the metal nanolayer is made of precious metals or transition metals.

12. A surface-enhanced Raman scattering (SERS) system, comprising:
    an analyte stage with a SERS-active structure of claim 1;
    a radiation source configured to irradiate the SERS-active structure to generate a plasmonic field; and
    a detector configured to detect Raman-scattered photons occurred in the plasmonic field.

13. A method for fabricating a surface-enhanced Raman scattering (SERS)-active structure, comprising the steps of:
    providing a substrate;
    disposing at least one metal nanoparticle on the substrate;
    forming a dielectric layer to cover the substrate and the at least one metal nanoparticle, wherein the dielectric layer comprises a recessed portion with a dihedral angle formed by a surface of the dielectric layer at which the at least one metal nanoparticle contacts the substrate; and
    forming a metal nanolayer to cover the dielectric layer, wherein the metal nanolayer comprises a gap located at and exposing the recessed portion.

14. The method of claim 13, wherein the step of disposing at least one metal nanoparticle on the substrate comprises:
    forming at least two polymer particles on the substrate, the at least two polymer particles being self-assembly and adjacent to each other, wherein an interspace exists between the at least two polymer particles;
    depositing a metal material to fill up the interspace;
    removing the at least two polymer particles; and
    annealing the metal material to transform the metal material into the at least one metal nanoparticle.

15. The method of claim 14, wherein the metal material is deposited to fill up the interspace using electron gun evaporator.

16. The method of claim 14, wherein the at least two polymer particles are polystyrene beads.

17. The method of claim 14, wherein the at least two polymer particles are a plurality of polymer particles, and the plurality of polymer particles are arranged in an array on the substrate.

18. The method of claim 13, wherein the dielectric layer is formed to cover the substrate and the at least one metal nanoparticle using atomic layer deposition.

19. The method of claim 13, wherein the dielectric layer is made of hafnium dioxide.

20. The method of claim 13, wherein the metal nanolayer is formed to cover the dielectric layer using electron gun evaporator.

* * * * *